(12) United States Patent
Lieu

(10) Patent No.: US 10,080,604 B2
(45) Date of Patent: Sep. 25, 2018

(54) ASEPTIC TRANSFER DEVICES, SYSTEMS, AND METHODS FOR MAINTAINING THE STERILITY OF SURGICAL INSTRUMENTS

(71) Applicant: COVIDIEN LP, Mansfield, MA (US)

(72) Inventor: Hung Lieu, Westminster, CO (US)

(73) Assignee: COVIDIEN LP, Mansfield, MA (US)

( * ) Notice: Subject to any disclaimer, the term of this patent is extended or adjusted under 35 U.S.C. 154(b) by 476 days.

(21) Appl. No.: 14/797,459

(22) Filed: Jul. 13, 2015

(65) Prior Publication Data

US 2016/0074096 A1 Mar. 17, 2016

Related U.S. Application Data

(60) Provisional application No. 62/050,470, filed on Sep. 15, 2014.

(51) Int. Cl.
*A61B 18/14* (2006.01)
*A61B 17/32* (2006.01)
(Continued)

(52) U.S. Cl.
CPC ...... *A61B 18/1445* (2013.01); *A61B 17/2909* (2013.01); *A61B 17/320092* (2013.01); *A61N 7/02* (2013.01); *A61B 17/320068* (2013.01); *A61B 2017/00734* (2013.01); *A61B 2017/2926* (2013.01); *A61B 2018/00178* (2013.01); *A61B 2018/1226* (2013.01);
(Continued)

(58) Field of Classification Search
CPC ............ A61B 18/1445; A61B 17/2909; A61B 17/320092; A61B 2090/0813; A61B 17/320068; A61B 2017/00734; A61B 2017/2926; A61B 2018/00178; A61B 2018/1226; A61B 2018/1455; A61B 2560/045; A61B 2560/0456; A61N 7/02
See application file for complete search history.

(56) References Cited

U.S. PATENT DOCUMENTS 4,641,076 A 2/1987 Linden
6,917,183 B2 7/2005 Barlev et al.
(Continued)

FOREIGN PATENT DOCUMENTS

WO 9806144 A1 2/1998
WO WO98/06144 * 2/1998 .............. H01M 2/02
WO 2007/090025 A1 8/2007

OTHER PUBLICATIONS

Extended European Search Report from European Appl. No. 15177220.9 dated Nov. 30, 2015.
(Continued)

*Primary Examiner* — Jaymi Della

(57) ABSTRACT

A method of transferring a battery assembly to a battery-powered surgical instrument includes releasably engaging a battery jacket with the battery assembly, transferring the battery jacket, having the battery assembly engaged thereto, to a battery-powered surgical instrument, and releasably engaging the battery jacket with a handle of the battery-powered surgical instrument such that the battery assembly is electrically coupled to the battery-powered surgical instrument and such that the battery jacket and the handle cooperate to enclose the battery assembly therein. Aseptic battery jackets for such use are also provided.

11 Claims, 9 Drawing Sheets

(51) Int. Cl.
　　　*A61B 17/29*　　　(2006.01)
　　　*A61N 7/02*　　　(2006.01)
　　　*A61B 17/00*　　　(2006.01)
　　　*A61B 18/12*　　　(2006.01)
　　　*A61B 90/00*　　　(2016.01)
　　　*A61B 18/00*　　　(2006.01)

(52) U.S. Cl.
　　　CPC ............... *A61B 2018/1455* (2013.01); *A61B 2090/0813* (2016.02); *A61B 2560/045* (2013.01); *A61B 2560/0456* (2013.01)

(56) References Cited

U.S. PATENT DOCUMENTS

| | | |
|---|---|---|
| 7,501,198 B2 | 3/2009 | Barlev et al. |
| 7,705,559 B2 | 4/2010 | Powell et al. |
| 8,400,108 B2 | 3/2013 | Powell et al. |
| 2003/0149424 A1* | 8/2003 | Barlev ............... H01M 2/1022 606/1 |
| 2003/0205987 A1 | 11/2003 | Barlev et al. |
| 2006/0206100 A1* | 9/2006 | Eskridge ............ A61B 17/1624 606/1 |
| 2007/0182369 A1* | 8/2007 | Gerber ................. H02J 7/0042 320/112 |
| 2010/0264876 A1 | 10/2010 | Powell et al. |
| 2012/0115007 A1* | 5/2012 | Felder ............... A61B 17/00234 429/121 |
| 2013/0009606 A1 | 1/2013 | Smith et al. |
| 2015/0088127 A1* | 3/2015 | Craig .................. A61B 19/026 606/41 |

OTHER PUBLICATIONS

European Examination Report issued in Appl. No. EP 15177220.9 dated Jun. 7, 2017.

* cited by examiner

ASEPTIC TRANSFER DEVICES, SYSTEMS, AND METHODS FOR MAINTAINING THE STERILITY OF SURGICAL INSTRUMENTS

CROSS REFERENCE TO RELATED APPLICATION

The present application claims the benefit of and priority to U.S. Provisional Application Ser. No. 62/050,470, filed on Sep. 15, 2014, the entire contents of which are incorporated herein by reference.

BACKGROUND

1. Technical Field

The present disclosure relates to aseptic battery transfer. More particularly, the present disclosure relates to devices, systems, and methods for the aseptic transfer of a battery assembly between a battery charger and surgical instrument while maintaining the sterility of the surgical instrument.

2. Background of Related Art

Battery-powered surgical instruments are advantageous in that they obviate the need for cables coupling the device to an electrical outlet or external power source. A typical rechargeable battery assembly for a battery-powered surgical instrument includes a housing containing one or more battery cells coupled to one another via a powering circuit through which the battery assembly is able to provide electrical power to the surgical instrument and receive electrical power from a charger.

Maintaining sterility in a surgical environment reduces the likelihood of infection and helps prevent the spread of disease. In order to maintain a sterile surgical environment, surgical instrumentation is sterilized and maintained in sterile condition prior to entering the sterile surgical environment. Reusable surgical instruments, or reusable components of surgical instruments, are thus required to be sterilized, e.g., via autoclaving, using a Sterrad® system, etc., after each use and/or prior to re-entering the sterile surgical environment.

Rechargeable battery assemblies require charging intermediately during use, after each use, or after several uses. Transfer of these rechargeable battery assemblies between the charging area and the surgical environment typically involves multiple transitions and/or points at which contamination may occur. Further, many of the rechargeable battery assemblies used in conjunction with surgical instrumentation are unfit for standard sterilization techniques, e.g., autoclaving. Accordingly, the ability to aseptically transfer the rechargeable battery assemblies between the charging area and the surgical environment is desirable.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with the present disclosure, a method of transferring a battery assembly to a battery-powered surgical instrument is provided. The method comprises releasably engaging a battery jacket with a battery assembly, transferring the battery jacket, having the battery assembly engaged thereto, to a battery powered surgical instrument, and releasably engaging the battery jacket with a handle of the battery-powered surgical instrument such that the battery assembly is electrically coupled to the battery-powered surgical instrument and such that the battery jacket and the handle cooperate to enclose the battery assembly therein.

In an aspect of the present disclosure, the method of releasably engaging the battery jacket with the battery assembly includes inserting the battery jacket about the battery assembly. In another aspect of the present disclosure, the battery jacket is releasably engaged about the battery assembly via a snap-fit engagement. In yet another aspect of the present disclosure, the method of releasably engaging the battery jacket with the battery assembly is performed while the battery assembly is operably coupled to a battery charging device. In still yet another aspect of the present disclosure, the battery jacket is inserted at least partially into the handle of the battery-powered surgical instrument and releasably engaged therein.

In another aspect of the present disclosure, the method of releasably engaging the battery jacket with the handle of the battery-powered surgical instrument sealingly encloses the battery assembly within the handle of the battery-powered surgical instrument. In yet another aspect of the present disclosure, the battery jacket is releasably engaged within the handle of the battery-powered surgical instrument via a snap-fit engagement. In still yet another aspect of the present disclosure, transferring the battery jacket to the battery-powered surgical instrument includes transferring the battery jacket from a non-sterile environment into a sterile environment.

In another aspect of the present disclosure, the method of transferring a battery assembly to a battery-powered surgical instrument further includes disengaging the battery jacket from the handle of the battery-powered surgical instrument, and withdrawing the battery jacket, having the battery assembly engaged therein, from the battery-powered surgical instrument.

In yet another aspect of the present disclosure, the method further includes transferring the battery jacket to a battery charging device, and manipulating the battery jacket to operably couple the battery assembly to the battery charging device. In another aspect of the present disclosure, the method further includes disengaging the battery jacket from about the battery assembly. In still yet another aspect of the present disclosure, the method further includes sterilizing the battery jacket.

A system is also provided in accordance with the present disclosure. The system comprises a battery-powered surgical instrument including a housing, a shaft extending distally from the housing, and an end effector assembly disposed at a distal end of the shaft. The housing includes a handle, a battery assembly, and a battery jacket defining an interior area configured to receive and releasably engage at least a portion of the battery assembly therein. The battery jacket is configured for insertion at least partially into the handle of the battery-powered surgical instrument in releasable engagement therewith to operably couple the battery assembly to the battery-powered surgical instrument and enclose the battery assembly therein.

The battery assembly of the system in the present disclosure may be a non-sterilizable, reusable component. Further, the battery jacket may be disposable or sterilizable.

In another aspect of the system of the present disclosure, the battery jacket includes at least one first engagement member and the battery assembly includes at least one second engagement member. The first and second engagement members are configured to releasably engage one another to releasably engage the battery jacket and battery assembly to one another upon insertion of the battery jacket about the batter assembly. Further, the first and second engagement members may be configured for releasable snap-fit engagement with one another.

In yet another aspect of the system of the present disclosure, the battery jacket defines a body portion having an open first end and a closed second end defining a lip. The battery jacket further includes a gasket disposed about the body portion adjacent the lip. The gasket is configured to sealingly engage the battery assembly between the battery jacket and the handle of the battery-powered surgical instrument upon releasable engagement of the battery jacket with the handle of the battery-powered surgical instrument. The system of the present disclosure may further include a battery charging device configured to operably couple to the battery assembly.

In another aspect of the system of the present disclosure, the battery jacket is configured to releasably engage with the battery assembly when the battery assembly is operably coupled to the battery charging device, without interrupting the operable coupling therebetween.

BRIEF DESCRIPTION OF THE DRAWINGS

Various aspects and features of the present disclosure are described herein with reference to the drawings wherein.

DETAILED DESCRIPTION

Figure 1:
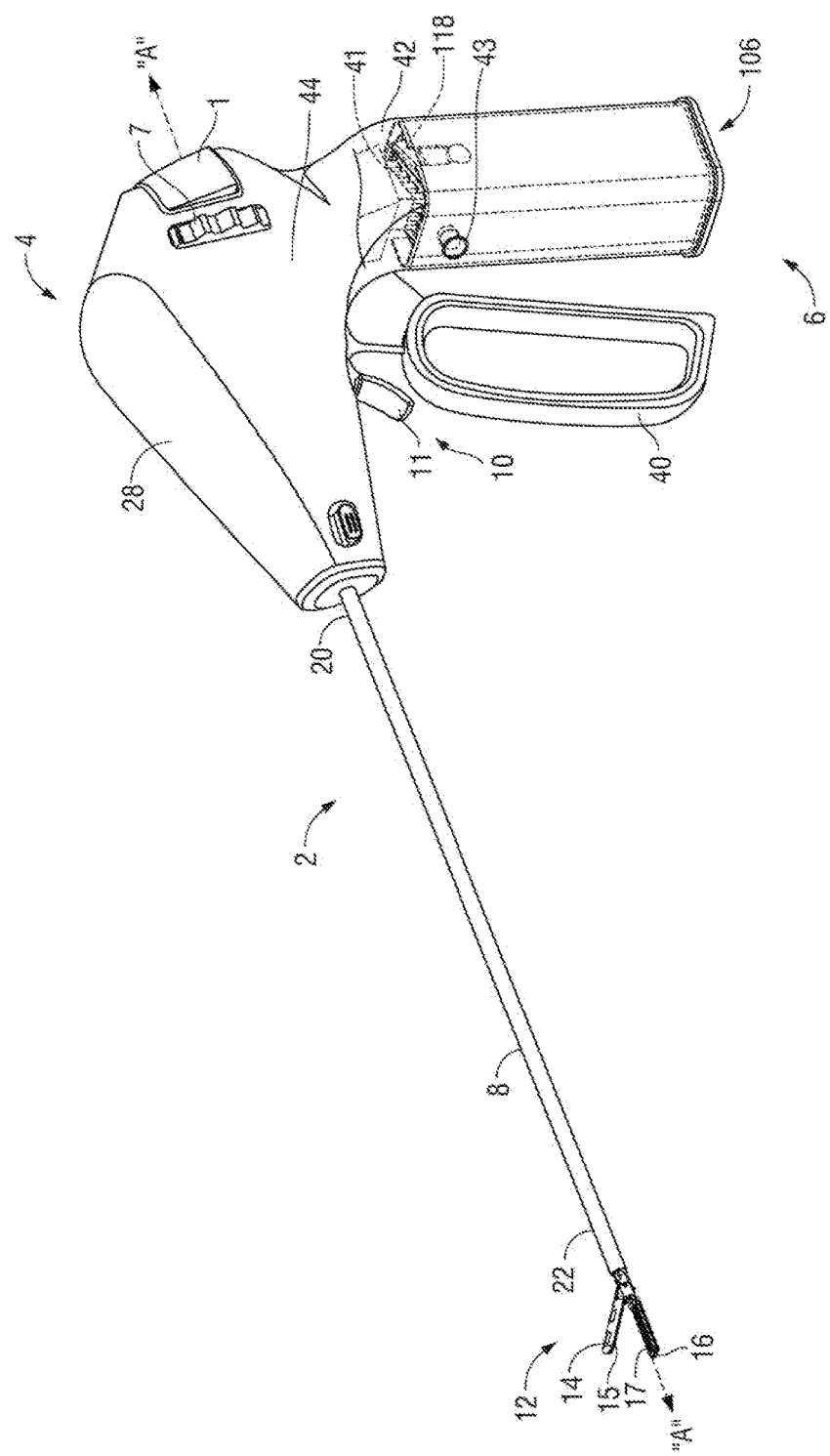
FIG. 1 is a side, perspective view of a portable, battery-powered surgical instrument configured for use in accordance with the present disclosure.
Figure 2:
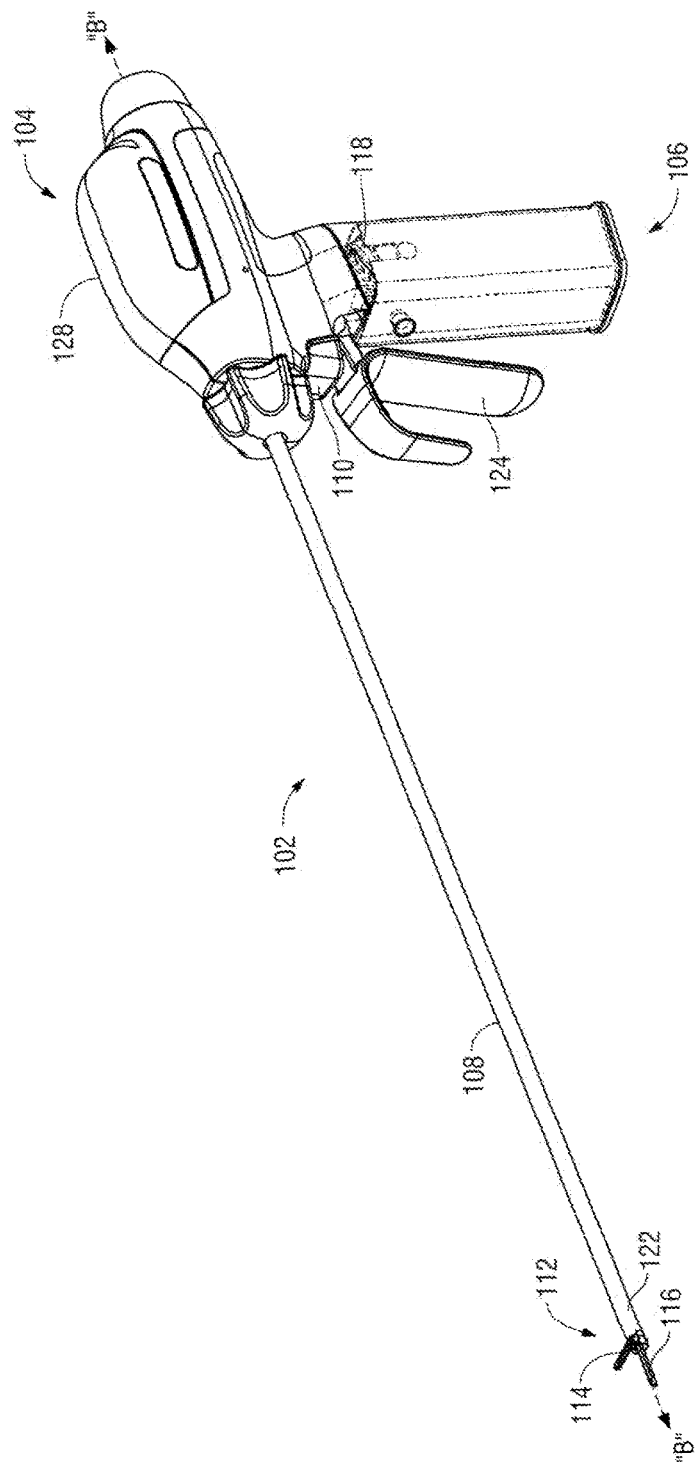
FIG. 2 is a side, perspective view of another portable, battery-powered surgical instrument configured for use in accordance with the present disclosure.

Referring now to FIGS. 1 and 2, FIG. 1 depicts an exemplary embodiment of a portable, battery-powered electrosurgical instrument 2 and FIG. 2 depicts an exemplary embodiment of a portable, battery-powered ultrasonic surgical instrument 102. For the purposes herein, either an electrosurgical instrument, e.g., instrument 2, an ultrasonic instrument, e.g., instrument 102, or any other suitable battery-powered device may be utilized in accordance with the present disclosure. Obviously, different considerations apply to each particular type of device; however, the features and aspects of the present disclosure are equally applicable and remain generally consistent with respect to any suitable battery-powered device. For the purposes herein, electrosurgical instrument 2 and ultrasonic instrument 102 are generally described.

With reference to FIG. 1, electrosurgical instrument 2, shown as an electrosurgical forceps, generally includes a housing 4, a battery assembly 118, an electrosurgical generator 28, a handle assembly 6, a rotating assembly 7, a shaft 8, a trigger assembly 10, a drive assembly (not shown), and an end effector assembly 12. End effector assembly 12 operatively connects to handle assembly 6 via the drive assembly (not shown) for imparting movement of one or both of jaw members 14, 16 of end effector assembly 12 between a spaced-apart position and an approximated position for grasping tissue therebetween.

Continuing with reference to FIG. 1, shaft 8 is coupled to housing 4 at proximal end 20 thereof and extends distally from housing 4 to define a longitudinal axis "A-A." End effector assembly 12, including jaw members 14 and 16, is disposed at a distal end 22 of shaft 8. End effector assembly 12 is shown configured as a unilateral assembly wherein jaw member 16 is fixed relative to shaft 8 and jaw member 14 is pivotable relative to jaw member 16 and shaft 8 between the spaced-apart and approximated positions. However, this configuration may be reversed, e.g., wherein jaw member 14 is fixed relative to shaft 8 and jaw member 16 is pivotable relative to jaw member 14 and shaft 8. Alternatively, end effector assembly 12 may be configured as a bilateral assembly, e.g., wherein both jaw members 14, 16 are pivotable relative to one another and shaft 8 between the spaced-apart and approximated positions.

Electrosurgical instrument 2 may be configured as a bipolar instrument. That is, each of the jaw members 14, 16 may include a respective conductive plate 15, 17 that is configured to function as an active (or activatable) and/or return electrode. Each conductive plate 15, 17 is electrically coupled to generator 28 via one or more electrical leads (not shown) that extend from generator 28, through shaft 8, and eventually coupling to one or both of conductive plates 15, 17 for conducting energy through tissue grasped therebetween. However, forceps 2 may alternatively be configured as a monopolar instrument.

Handle assembly 6 includes a moveable handle 40 that is movable relative to a fixed handle portion 42 of housing 4 for moving jaw members 14, 16 of end effector assembly 12 between the spaced-apart and approximated positions. Rotating assembly 7 is rotatable in either direction about longitudinal axis "A-A" to rotate shaft 8 and, thus, end effector assembly 12 about longitudinal axis "A-A." Trigger assembly 10 is in operable communication with a knife assembly (not shown) including a knife blade (not shown) that is selectively translatable between jaw members 14, 16 to cut tissue grasped therebetween, e.g., upon actuation of trigger 11 of trigger assembly 10.

With continued reference to FIG. 1, housing 4 is configured to operably engage electrosurgical generator 28 and battery assembly 118. Generator 28 is releasably engagable with body portion 44 of housing 4, while battery assembly 118 is releasably engagable within fixed handle portion 42 of housing 4 via the use of battery jacket 200 (FIG. 5), as detailed below. More specifically, battery jacket 200 (FIG. 5), having battery assembly 118 disposed therein, is configured for insertion into and engagement with fixed handle portion 42 of housing 4 such that battery assembly 118 is operably engaged within fixed handle portion 42. When battery assembly 118 is operably engaged within fixed handle portion 42, the plurality of contacts 182 (FIG. 3) of battery assembly 118 electrically couple with electrical contacts 41 of generator 28. Generator 28 releasably engages body portion 44 of housing 4 and may be selectively removable from body portion 44 either in connection with the removal battery assembly 118 or independently.

When forceps 2 is assembled, generator 28 is disposed in operable communication with battery assembly 118, e.g., via coupling of contacts 41 and 182 (FIG. 3), to provide electrosurgical energy to end effector 12 for electrosurgically treating tissue, although forceps 2 may alternatively be configured to deliver any other suitable form of energy to tissue, e.g., thermal energy, microwave energy, light energy, etc. With respect to electrosurgical tissue treatment, generator 28 may include suitable electronics that convert the electrical energy from battery assembly 118 into an RF energy waveform to energize one or both of jaw members 14, 16. That is, generator 28 may be configured to transmit RF energy to conductive plate 15 of jaw member 14 and/or conductive plate 17 of jaw member 16 to conduct energy therebetween for treating tissue. Activation switch 1 disposed on housing 4 is activatable for selectively enabling generator 28 to generate and subsequently transmit RF energy to conductive plate 15 and/or conductive plate 17 of jaw members 14, 16, respectively, for treating tissue grasped therebetween.

Referring now to FIG. 2, ultrasonic instrument 102 includes components similar to that of forceps 2 shown in FIG. 1, namely, a housing 104, a battery assembly 118, a generator 128, a handle assembly 106, a shaft 108, and an end effector assembly 112. Accordingly, only the differences between ultrasonic instrument 102 and forceps 2 (FIG. 1) will be described in detail below.

Housing 104 is configured to releasably engage ultrasonic generator 128 and releasably receive battery assembly 118 (via the use of battery jacket 200 (FIG. 5)). Shaft 108 extends distally from housing 104 to define longitudinal axis "B-B" and includes end effector assembly 112 disposed at distal end 122 thereof. One or both of jaw members 114 and 116 of end effector assembly 112 are movable relative to one another, e.g., upon actuation of moveable handle 124, between an open position and a clamping position for grasping tissue therebetween. Further, one of the jaw members, e.g., jaw member 116, serves as an active or oscillating ultrasonic blade that is selectively activatable to ultrasonically treat tissue grasped between jaw members 114, 116.

Generator 128 includes a transducer (not shown) configured to convert electrical energy provided by battery assembly 118 into mechanical energy that produces motion at the end of a waveguide, e.g., at blade 116. More specifically, the electronics (not explicitly shown) of the generator 128 convert the electrical energy provided by battery assembly 118 into a high voltage AC waveform that drives the transducer (not shown). When the transducer (not shown) and the waveguide are driven at their resonant frequency, mechanical, e.g., ultrasonic, motion is produced at the active jaw member, e.g., jaw member 116 for treating tissue grasped between jaw members 114, 116. Further, an activation button 110 disposed on housing 104 is selectively activatable to operate instrument 102 in two modes of operation: a low-power mode of operation and a high-power mode of operation.

Figure 3:
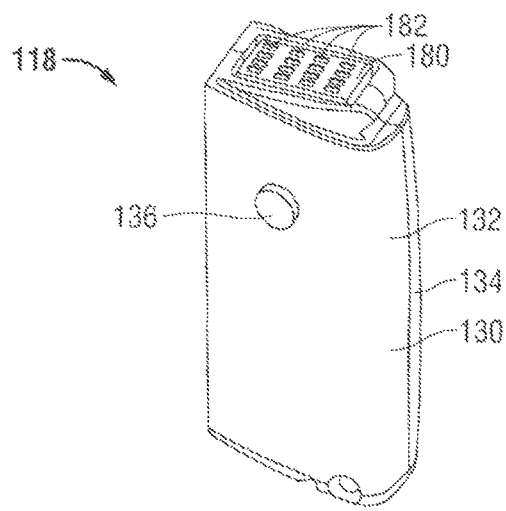
FIG. 3 is a side, perspective view of an exemplary battery assembly provided in accordance with the present disclosure and configured for use with either or both of the instruments of FIGS. 1 and 2.
Figure 4:
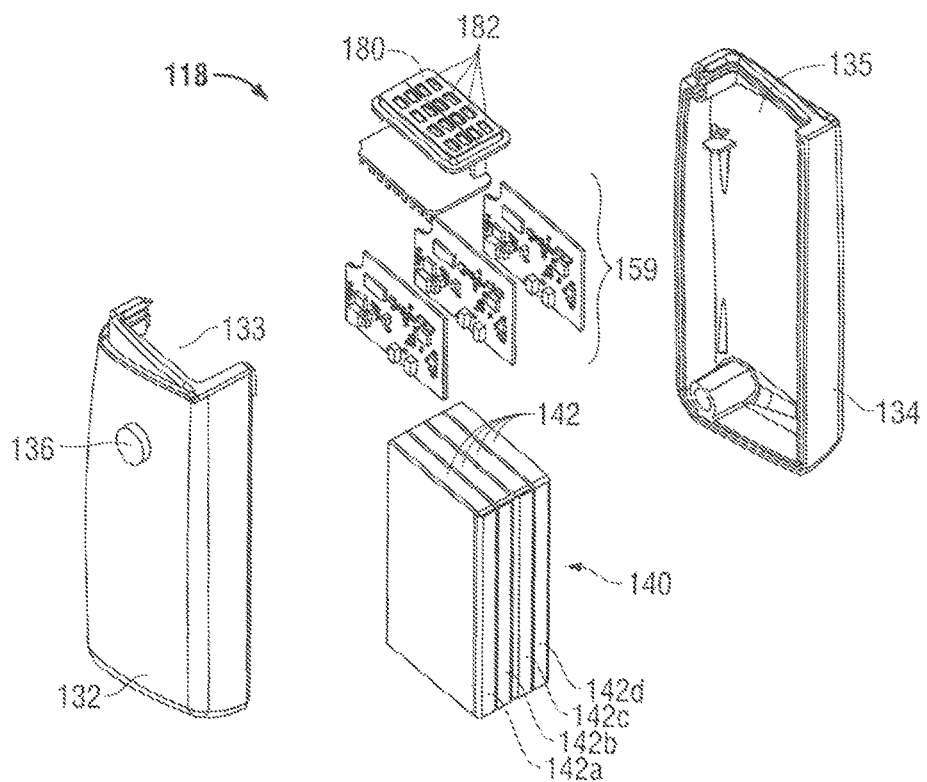
FIG. 4 is an exploded, perspective view of the battery assembly of FIG. 3.

With reference to FIGS. 3 and 4, battery assembly 118 generally includes an outer housing 130, a battery pack 140, battery circuitry 159, and a contact cap 180. Outer housing 130 of battery assembly 118 is formed from first and second housing parts 132, 134 that cooperate to house battery pack 140 and battery circuitry 159. Housing parts 132, 134 contain nubs 136 configured to engage with a corresponding notch 203 (FIG. 5) on sterile battery jacket 200 (FIG. 5), as detailed below, although other suitable engagement features are also contemplated. Housing parts 132, 134 define cutouts 133, 135, respectively, that cooperate to form a window configured to retain contact cap 180. Contact cap 180 is electrically coupled to battery circuitry 159, which, in turn, is electrically coupled to battery pack 140. Contact cap 180 includes a plurality of contacts 182 configured to provide an electrical interface between battery assembly 118, e.g., battery pack 140 and battery circuitry 159, and the corresponding battery-powered surgical instrument to which battery assembly 118 is coupled, e.g., electrosurgical instrument 2 (FIG. 1) or ultrasonic instrument 102 (FIG. 2), as well as a battery charging device, e.g., charging assembly 300 (FIG. 6), for transmitting power and/or control signals therebetween. Battery pack 140 includes one or more battery cells 142, e.g., four (4) battery cells 142a-142d, although greater or fewer battery cells 142a-142d are also contemplated.

Figure 5:
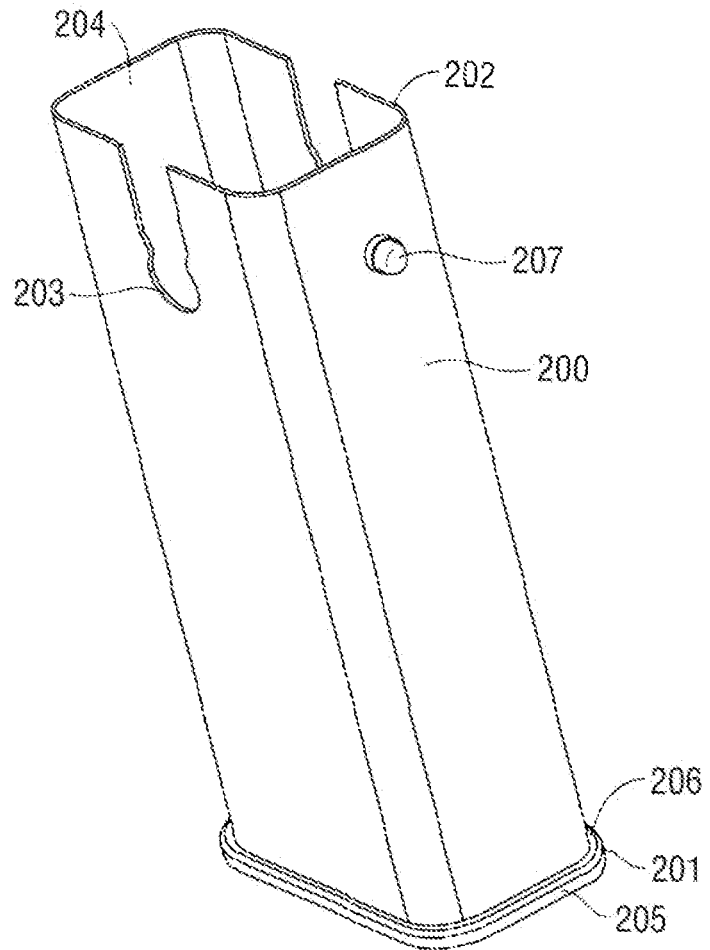
FIG. 5 is a perspective view of an exemplary battery jacket provided in accordance with the present disclosure and configured for use with the battery assembly of FIG. 3 or any other suitable battery assembly to facilitate aseptic transfer thereof.

Turning now to FIG. 5, with respect to the sterilization of battery assemblies, it has been found that the risk of thermal runaway and/or other damage is increased in instances where the state of charge of the battery assembly approaches 100%, e.g., when the battery is fully or near-fully charged. Thus, after use, it is desirable to sterilize the battery assembly prior to charging the battery assembly, rather than the other way around. However, sterilizing the battery assembly prior to charging the battery assembly requires that the battery assembly be maintained in a sterile condition during the charging process. Such is also the case where re-charging of the battery assembly is required during a surgical procedure. Accordingly, the present disclosure provides battery jackets configured to facilitate the transfer of an unsterilized battery assembly to a sterilized surgical instrument for use therewith without compromising the sterile field. That is, the battery jackets provided herein allow for an unsterilized battery assembly and/or a battery assembly that has been charged in an unsterilized environment, to be transferred and used in a sterile environment without the risk of contamination.

Continuing with reference to FIG. 5, and with additional reference to FIG. 3, battery jacket 200 includes a closed distal end 201 and an open proximal end 202. Battery jacket 200 defines a hollow interior 204 accessible through the open proximal end 202 that is configured to receive battery assembly 118 (FIG. 3) or other suitable battery assembly. In embodiments, battery jacket 200 defines a length dimension equal to or greater than that of battery assembly 118 to enable full receipt of battery assembly 118 therein. Further, battery jacket 200 is shaped to complement battery assembly 118 to securely retain battery assembly 118 within battery jacket 200. The open proximal end 202 of battery jacket 200 enables contact cap 180 of battery assembly 118 to remain exposed once battery assembly 118 is inserted therein. As noted above, contact cap 180 includes contacts 182 that provide an electrical interface between battery assembly 118 and both the battery-powered surgical instrument and the battery charging device for transmitting power and/or control signals therebetween.

Battery jacket 200 is made from a sterilizable metal or other suitable material, e.g. thermoplastics such as polycarbonate and low-density polyethylene (LDPE), Udel®, Ultem®, ABS etc. In one embodiment, battery jacket 200 can be reused and sterilized in the same methods, and in the same package, as reusable surgical instruments, or reusable components of surgical instruments, e.g. via autoclaving or using a Sterrad® system, after each use and/or prior to re-entering the sterile surgical environment. In other embodiments, battery jacket 200 can be disposable or sterilizable separately.

Figure 9:
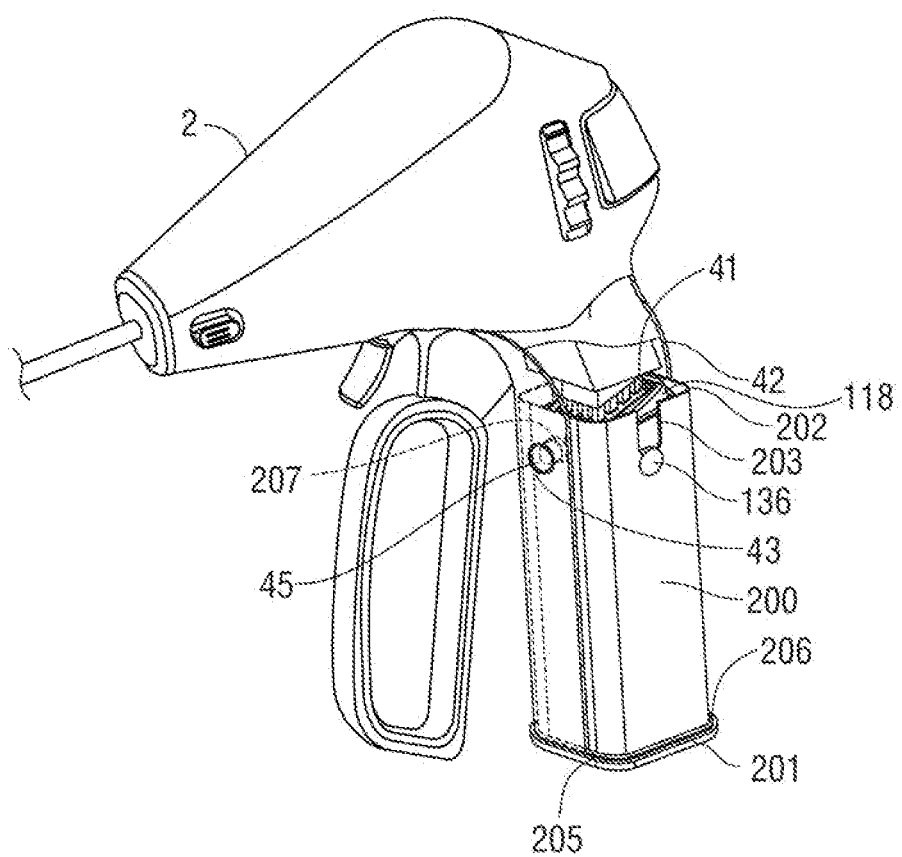
FIG. 9 is a perspective, partial cut-away view illustrating the battery-powered surgical instrument of FIG. 1 having the battery jacket of FIG. 5, with the battery assembly of FIG. 3 engaged therein, operably coupled to the surgical instrument.
Figure 10:
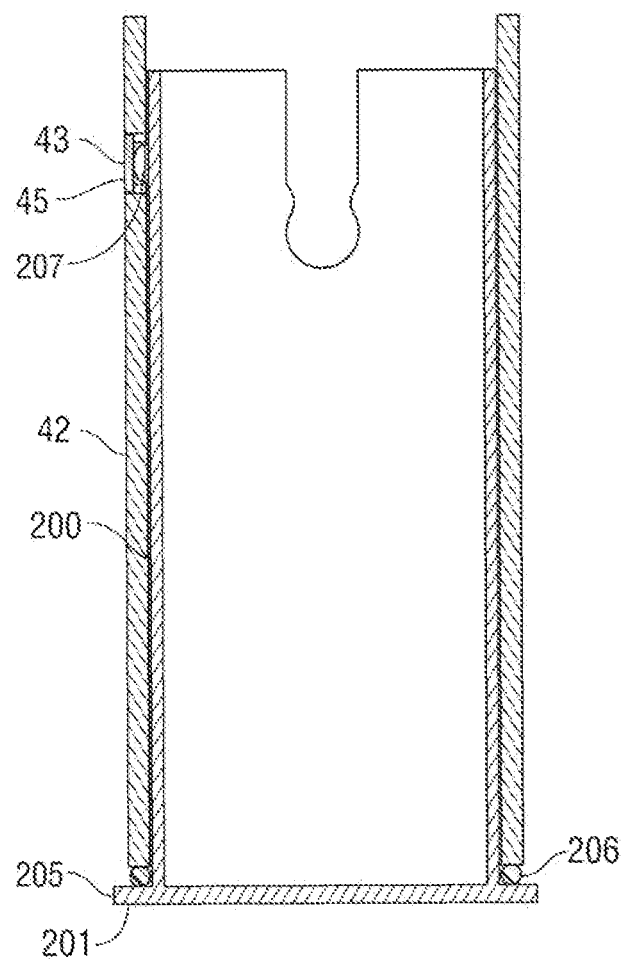
FIG. 10 is a transverse, cross-sectional view of the handle of the battery-powered surgical instrument of FIG. 1 having the battery jacket of FIG. 5, with the battery assembly of FIG. 3 engaged therein, operably coupled within the handle.

With additional reference to FIGS. 9 and 10, in embodiments, one or more locking member(s) 207 are disposed on the exterior surface of battery jacket 200. Each locking member 207 is configured to releasably engage a corresponding locking slot 43 defined on the interior surface of fixed handle 42 of surgical instrument 2 (FIG. 1). In embodiments, locking member 207 may be spring loaded to facilitate the engagement and disengagement from locking slot 43 of fixed handle 42. In use, locking member 207 is initially compressed upon insertion of battery jacket 200 and battery assembly 118 into fixed handle 42. When battery jacket 200 and battery assembly 118 are fully inserted into fixed handle 42 and locking member 207 is aligned with locking slot 43, locking tab 207 is permitted to return to its at-rest or initial position, wherein locking member 207 extends through slot 43 and is engaged therein under bias. Locking slot 43 consists of a moveable membrane 45 that allows a user to compress locking member 207, allowing battery jacket 200 and battery assembly 118 to be disengaged and subsequently removed from fixed handle portion 42. Other configurations of releasable locking features to releasably secure battery jacket 200 and battery assembly 118 within fixed handle portion 42 are also contemplated.

Referring again to FIGS. 3 and 5, battery jacket 200 further contains a locking mechanism to removably engage battery assembly 118 within battery jacket 200 upon insertion of battery jacket 200 about battery assembly 118. In embodiments, the locking mechanism includes a notch 203 defined within battery jacket 200 that is configured to engage a corresponding nub 136 of battery assembly 118 to lock battery jacket 200 about battery assembly 118. More specifically, upon insertion of battery jacket 200 about battery assembly 118 and upon application of sufficient urging thereto, nub 136 urges battery jacket 200 to flex to expand notch 203 and permit the corresponding nub 136 to pass through the reduced-diameter portion of notch 203 and be seated therein, e.g., via snap-fit engagement. Once nub 136 is seated or snap-fit into notch 203, battery jacket 200 is permitted to return to its at-rest position, retaining nub 136 therein such that battery assembly 118 is securely retained within battery jacket 200. Likewise, when sufficient urging is used to withdraw battery assembly 118 from battery jacket 200, nub 136 causes battery jacket 200 to flex to expand notch 203 and permit withdrawal of nub 136 from notch 203, thereby disengaging battery jacket from battery assembly 118. Battery jacket 200 may further include a raised portion (not shown) disposed about notch 203 to inhibit exposure of nub 136 of battery assembly 118 when battery assembly 118 is received within battery jacket 200. Further, although a notch and nub locking mechanism is provided, other configurations of locking mechanisms are also contemplated.

With reference to FIG. 5, battery jacket 200 further contains a raised lip 205 extending about the exterior of the closed distal end 201 thereof. A gasket 206 is disposed on raised lip 205 and about the body of battery jacket 200. Upon engagement of battery jacket 200 with fixed handle portion 42 (FIG. 10), gasket 206 is compressed between the free end of fixed handle portion 42 (FIG. 10) and raised lip 205 to establish a fluid-tight seal between battery jacket 200 and fixed handle portion 42, thus inhibiting the passage of fluids therebetween.

Figure 6:
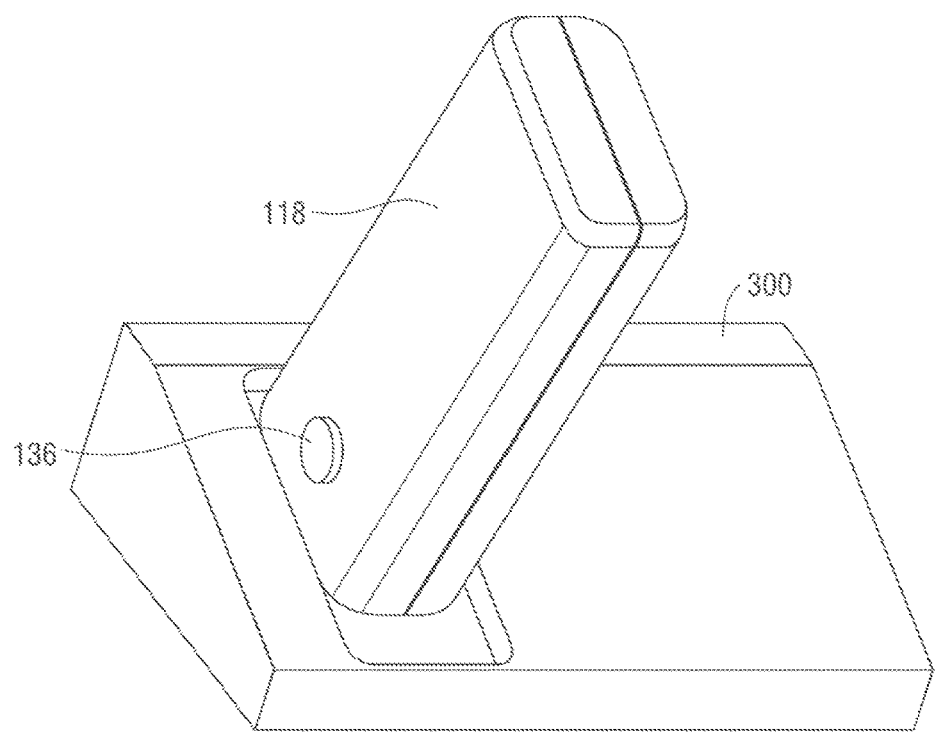
FIG. 6 is a perspective view of the battery assembly of FIG. 3 coupled to a charging assembly for charging the battery assembly.
Figure 7:
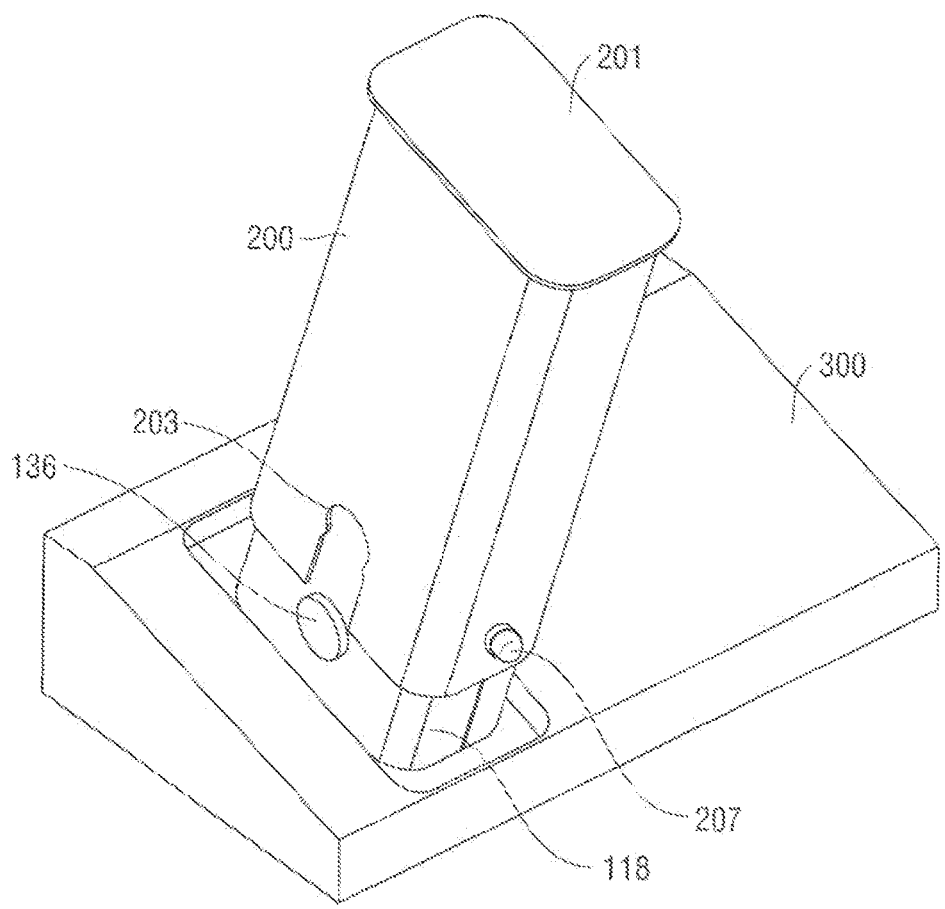
FIG. 7 is a perspective view illustrating the battery jacket of FIG. 5 being inserted about the battery assembly of FIG. 3 with the battery assembly coupled to the charging assembly of FIG. 6.
Figure 8:
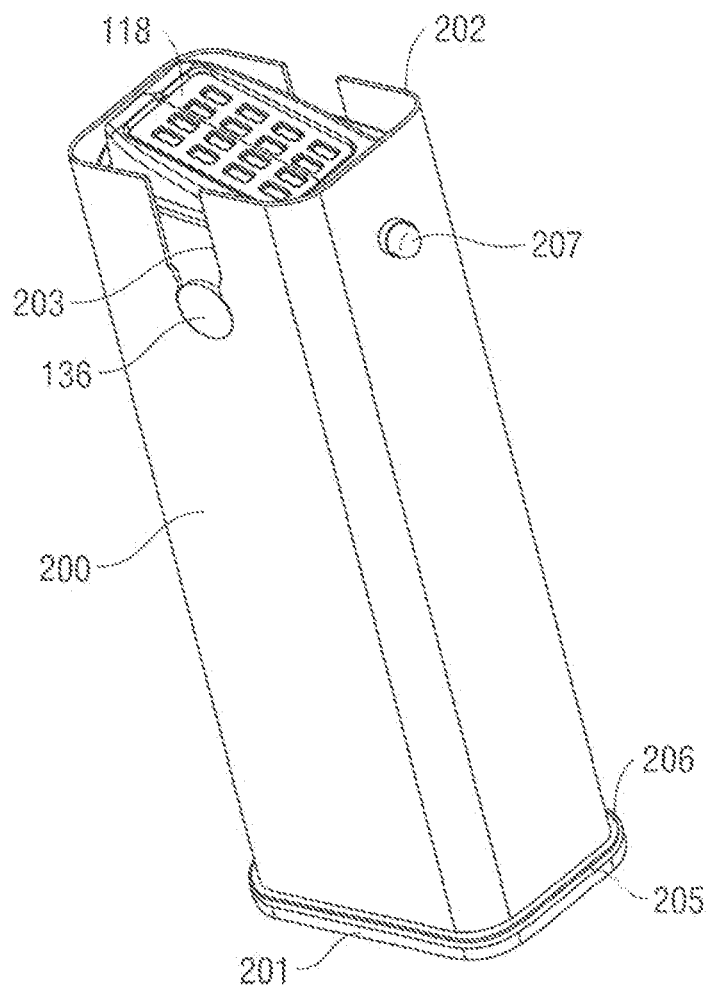
FIG. 8 is a perspective view of the battery assembly of FIG. 3 engaged within the battery jacket of FIG. 5.

Referring to FIGS. 6-8, and initially to FIG. 6, battery assembly 118 is shown operably coupled to a charging assembly 300. Although shown engaged with charging assembly 300, the following also applies to instances where battery assembly 118 is coupled to a staging bay or other holding device.

Referring to FIGS. 7 and 8, it can be appreciated that battery jacket 200 can be inserted about battery assembly 118 and engaged therewith, as detailed above, without the need to touch or directly contact battery assembly 118 and/or charging assembly 300. Once battery jacket 200 is snapped, or locked, in engagement about battery assembly 118, battery jacket 200 can be manipulated to decouple and remove battery assembly 118 from the charging assembly 300. Thereafter, battery jacket 200, with battery assembly 118 engaged therein as shown in FIG. 8, can be transferred into a sterile surgical arena and, ultimately, engaged with surgical instrument 2 (FIG. 1) without the risk of contamination.

Referring to FIGS. 8-10, in order to engage battery jacket 200, with battery assembly 118 disposed therein, with surgical instrument 2, battery jacket 200 is inserted into fixed handle portion 42 of surgical instrument 2 until locking member 207 is engaged within locking slot 43, thereby securing battery jacket 200 and battery assembly 118 within fixed handle portion 42 of surgical instrument 2 such that contacts 182 of battery assembly 118 are disposed in communication with the contacts 41 of generator 28 of surgical instrument 2 and such that gasket 206 is compressed between raised lip 205 of sterile battery jacket 200 and fixed handle portion handle 42 of electrosurgical instrument 2 to establish a fluid-tight seal therebetween.

Release of the locking mechanism, e.g., via compression of locking member 207, may allow battery assembly 118 and sterile battery jacket 200 to slide out by gravity, thus enabling removal of battery assembly 118 and sterile battery jacket 200. Alternatively, a spring mechanism (not shown) may be provided to provide sufficient urging upon release of locking mechanism to eject battery assembly 118 and sterile battery jacket 200. In either configuration, once removed, sterile battery jacket 200 may be removed from battery assembly 118 and discarded or sterilized for reuse use, while battery assembly 118 is connected to a charger or other suitable device for recharging, storage, updating, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A method comprising:
 releasably engaging a battery jacket with a battery assembly while the battery assembly is operably coupled to a battery charging device;
 transferring the battery jacket, having the battery assembly engaged thereto, from the battery charging device to a battery-powered surgical instrument; and releasably engaging the battery jacket with a handle of the battery-powered surgical instrument such that the battery assembly is electrically coupled to the battery-powered surgical instrument and such that the battery jacket and the handle cooperate to enclose the battery assembly therein.

2. The method according to claim 1, wherein releasably engaging the battery jacket with the battery assembly includes inserting the battery jacket about the battery assembly.

3. The method according to claim 2, wherein the battery jacket is releasably engaged about the battery assembly via a snap-fit engagement.

4. The method according to claim 1, wherein the battery jacket is inserted at least partially into the handle of the battery-powered surgical instrument and releasably engaged therein.

5. The method according to claim 1, wherein releasably engaging the battery jacket with the handle of the battery-powered surgical instrument sealingly encloses the battery assembly within the handle of the battery-powered surgical instrument.

6. The method according to claim 1, wherein the battery jacket is releasably engaged within the handle of the battery-powered surgical instrument via a snap-fit engagement.

7. The method according to claim 1, wherein transferring the battery jacket to the battery-powered surgical instrument includes transferring the battery jacket from a non-sterile environment into a sterile environment.

8. The method according to claim 1, further including:
disengaging the battery jacket from the handle of the battery-powered surgical instrument; and
withdrawing the battery jacket, having the battery assembly engaged therein, from the battery-powered surgical instrument.

9. The method according to claim 8, further including:
transferring the battery jacket to the battery charging device; and
manipulating the battery jacket to operably couple the battery assembly to the battery charging device.

10. The method according to claim 9, further including disengaging the battery jacket from about the battery assembly.

11. The method according to claim 10, further including sterilizing the battery jacket.

\* \* \* \* \*